US005536637A

United States Patent [19]

Jacobs

[11] Patent Number: 5,536,637
[45] Date of Patent: Jul. 16, 1996

[54] METHOD OF SCREENING FOR CDNA ENCODING NOVEL SECRETED MAMMALIAN PROTEINS IN YEAST

[75] Inventor: Kenneth Jacobs, Newton, Mass.

[73] Assignee: Genetics Institute, Inc., Cambridge, Mass.

[21] Appl. No.: 328,962

[22] Filed: Oct. 24, 1994

Related U.S. Application Data

[63] Continuation of Ser. No. 45,267, Apr. 7, 1993, abandoned.

[51] Int. Cl.[6] .................................................. C12Q 1/68
[52] U.S. Cl. .......................... 435/6; 435/69.7; 435/69.8; 435/172.3; 435/91.4; 435/203; 435/201; 435/22
[58] Field of Search .................... 935/9, 13, 80; 435/29, 69.1, 69.7, 69.8, 172.3, 320.1, 6, 91.4, 22, 201, 203

[56] References Cited

U.S. PATENT DOCUMENTS 5,037,760  8/1991  Smith et al. ......................... 435/320.1

OTHER PUBLICATIONS

Smith et al., Journal of Bacteriology 169(7):3321–3328 (1987).
Kaiser et al., Science 235:312–317 (1987).
Sidhu, et al., Gene 107:111–118 (1991).
Bird, et al., The Journal of Cell Biology 105:2905–2914 (1987).
Ferenci, et al., Journal of Bacteriology 169(12):5339–5342 (1987).
Zhang, et al., Molecular Microbiology 3(10):1361–1369 (1989).
Davies, Tree 3(4); Tibtech 6(4) (1988).
E. Martegani et al. EMBO J. 11(6):2151–2157 1992.
G. B. Segel et al. PNAS 89:6060–4 Jul. 1992.
J. K. Ngsee et al. Gene 86:251–5 1990.
C A Kaiser et al Science 235:312–7 Jan. 16, 1987.

*Primary Examiner*—Stephen G. Walsh
*Assistant Examiner*—Lorraine M. Spector
*Attorney, Agent, or Firm*—Scott A. Brown; Patricia A. McDaniels; Thomas J. DesRosier

[57] ABSTRACT

A novel method of screening for novel secreted mammalian proteins is described in which mammalian secretory leader sequences are detected using the yeast invertase gene as a reporter system.

1 Claim, No Drawings

5,536,637

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1542 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Saccharomyces cerevisiae ( v i i ) IMMEDIATE SOURCE:
        ( B ) CLONE: SUC2

( x i ) SEQUENCE DESCRIPTION: SEQ ID NO:1:

```
TCAATGACAA ACGAAACTAG CGATAGACCT TTGGTCCACT TCACACCCAA CAAGGGCTGG      60
ATGAATGACC CAAATGGGTT GTGGTACGAT GAAAAAGATG CCAAATGGCA TCTGTACTTT     120
CAATACAACC CAAATGACAC CGTATGGGGT ACGCCATTGT TTTGGGGCCA TGCTACTTCC     180
GATGATTTGA CTAATTGGGA AGATCAACCC ATTGCTATCG CTCCCAAGCG TAACGATTCA     240
GGTGCTTTCT CTGGCTCCAT GGTGGTTGAT TACAACAACA CGAGTGGGTT TTTCAATGAT     300
ACTATTGATC CAAGACAAAG ATGCGTTGCG ATTTGGACTT ATAACACTCC TGAAAGTGAA     360
GAGCAATACA TTAGCTATTC TCTTGATGGT GGTTACACTT TTACTGAATA CCAAAAGAAC     420
CCTGTTTTAG CTGCCAACTC CACTCAATTC AGAGATCCAA AGGTGTTCTG GTATGAACCT     480
TCTCAAAAAT GGATTATGAC GGCTGCCAAA TCACAAGACT ACAAAATTGA AATTTACTCC     540
TCTGATGACT TGAAGTCCTG GAAGCTAGAA TCTGCATTTG CCAACGAAGG TTTCTTAGGC     600
TACCAATACG AATGTCCAGG TTTGATTGAA GTCCCAACTG AGCAAGATCC TTCCAAATCT     660
TATTGGGTCA TGTTTATTTC TATCAACCCA GGTGCACCTG CTGGCGGTTC CTTCAACCAA     720
TATTTGTTG GATCCTTCAA TGGTACTCAT TTTGAAGCGT TTGACAATCA ATCTAGAGTG     780
GTAGATTTTG GTAAGGACTA CTATGCCTTG CAAACTTTCT TCAACACTGA CCCAACCTAC     840
GGTTCAGCAT TAGGTATTGC CTGGGCTTCA AACTGGGAGT ACAGTGCCTT TGTCCCAACT     900
AACCCATGGA GATCATCCAT GTCTTTGGTC CGCAAGTTTT CTTTGAACAC TGAATATCAA     960
GCTAATCCAG AGACTGAATT GATCAATTTG AAAGCCGAAC CAATATTGAA CATTAGTAAT    1020
GCTGGTCCCT GGTCTCGTTT TGCTACTAAC ACAACTCTAA CTAAGGCCAA TTCTTACAAT    1080
GTCGATTTGA GCAACTCGAC TGGTACCCTA GAGTTTGAGT TGGTTTACGC TGTTAACACC    1140
ACACAAACCA TATCCAAATC CGTCTTTGCC GACTTATCAC TTTGGTTCAA GGGTTTAGAA    1200
GATCCTGAAG AATATTTGAG AATGGGTTTT GAAGTCAGTG CTTCTTCCTT CTTTTTGGAC    1260
CGTGGTAACT CTAAGGTCAA GTTTGTCAAG GAGAACCCAT ATTTCACAAA CAGAATGTCT    1320
GTCAACAACC AACCATTCAA GTCTGAGAAC GACCTAAGTT ACTATAAAGT GTACGGCCTA    1380
CTGGATCAAA ACATCTTGGA ATTGTACTTC AACGATGGAG ATGTGGTTTC TACAAATACC    1440
TACTTCATGA CCACCGGTAA CGCTCTAGGA TCTGTGAACA TGACCACTGG TGTCGATAAT    1500
TTGTTCTACA TTGACAAGTT CCAAGTAAGG GAAGTAAAAT AG                      1542
```

METHOD OF SCREENING FOR CDNA ENCODING NOVEL SECRETED MAMMALIAN PROTEINS IN YEAST

This application is a continuation of application Ser. No. 08/045,267, filed Apr. 7, 1993, now abandoned.

The present invention relates to a novel method of cloning cDNAs which encode cytokines, to novel cDNAs isolated by the method, and to novel secreted proteins encoded by the cDNAs.

BACKGROUND OF THE INVENTION

Cytokines are secreted proteins which act on specific hematopoietic target cells to cause a differentiation event or on other target cells to induce a particular physiological response, such as secretion of proteins characteristic of inflammation. Cytokines, also variously known as lymphokines, hematopoietins, interleukins, colony stimulating factors, and the like, can be important therapeutic agents, especially for diseases or conditions in which a specific cell population is depleted. For example, erythropoietin, G-CSF, and GM-CSF, have all become important for treatment of anemia and leukopenia, respectively. Other cytokines such as interleukin-3, interleukin-6 and interleukin-11 show promise in treatment of conditions such as thrombocytopenia.

For these reasons a significant research effort has been expended in searching for novel cytokines and cloning the DNAs which encode them. In the past, novel cytokines were identified by assaying a particular cell such as a bone marrow cell, for a measurable response, such as proliferation. The search for novel cytokines has thus been limited by the assays available, and if a novel cytokine has an activity which is unmeasurable by a known assay, the cytokine remains undetectable. In a newer approach, cDNAs encoding cytokines have been detected using the polymerase chain reaction (PCR) and oligonucleotide primers having homology to shared motifs of known cytokines or their receptors. The PCR approach is also limited by the necessity for knowledge of previously cloned cytokines in the same protein family. Cytokines have also been cloned using subtractive hybridization to construct and screen cDNA libraries, or they can potentially be cloned using PCR followed by gel electrophoresis to detect differentially expressed genes. The subtractive hybridization methods are based on the assumption that cytokine mRNAs are those that are differentially expressed, and these methods do not require any prior knowledge of the sequence of interest. However, many cytokines may be encoded by mRNAs which are not differentially expressed, and thus are undetectable using these methods.

SUMMARY OF THE INVENTION

In one embodiment, the present invention is directed to a method for isolating a cDNA encoding a novel secreted mammalian protein which comprises:

a) constructing a cDNA library from mammalian cellular RNA;

b) ligating said cDNA library to a DNA encoding a nonsecreted yeast invertase;

c) transforming the ligated DNA into *E. coli*;

d) isolating DNA containing mammalian cDNA ligated to the DNA encoding the nonsecreted yeast invertase from the transformed *E. coli* of step c);

e) transforming the DNA of step d) into a yeast cell which does not contain an invertase gene;

f) selecting transformed yeast cells (from step e) which are capable of growth on sucrose or raffinose;

g) purifying DNA from the yeast cells of step f);

h) analyzing the DNA obtained from step g) to determine its sequence and to determine whether it contains a novel sequence;

i) preparing a second cDNA library from mammalian cellular RNA and screening said second cDNA library to detect a full-length cDNA which contains the novel sequence of step h);

j) isolating the full-length cDNA of step i).

In another embodiment, the invention is directed to a cDNA encoding a secreted protein isolated using the method of:

a) constructing a cDNA library from mammalian cellular RNA;

b) ligating said cDNA library to a DNA encoding a nonsecreted yeast invertase;

c) transforming the ligated DNA into *E. coli*;

d) isolating DNA containing mammalian cDNA ligated to the DNA encoding the nonsecreted yeast invertase from the transformed *E. coli* of step c);

e) transforming the DNA of step d) into a yeast cell which does not contain an invertase gene;

f) selecting yeast cells capable of growth on sucrose or raffinose;

g) purifying DNA from the yeast cells of step f);

h) analyzing the DNA obtained from step g) to determine its sequence and to determine whether it contains a novel sequence;

i) screening a second cDNA library to detect a full-length cDNA which contains the novel sequence of step h);

j) isolating the full-length cDNA of step i).

In yet another embodiment the invention comprises a secreted protein isolated by the steps of:

a) constructing a cDNA library from mammalian cellular RNA;

b) ligating said cDNA library to a DNA encoding a nonsecreted yeast invertase;

c) transforming the ligated DNA into *E. coli*;

d) isolating DNA containing mammalian cDNA ligated to the DNA encoding the nonsecreted yeast invertase from the transformed *E. coli* of step c);

e) transforming the DNA of step d) into a yeast cell which does not contain an invertase gene;

f) selecting yeast cells capable of growth on sucrose or raffinose;

g) purifying DNA from the yeast cells of step f);

h) analyzing the DNA obtained from step g) to determine its sequence and to determine whether it contains a novel sequence;

i) screening a second cDNA library to detect a full-length cDNA which contains the novel sequence of step h);

j) isolating the full-length cDNA of step i).

DETAILED DESCRIPTION OF THE INVENTION

In order to use sucrose or raffinose as a carbon and energy source, yeast such as *Saccharomyces cerevisiae* must secrete the enzyme invertase, which cleaves sucrose to yield fructose and glucose and which cleaves raffinose to yield sucrose and melibiose. A large number of known mammalian secretory leader sequences can mediate secretion of yeast invertase. In accordance with the present invention, therefore, mammalian cDNA libraries are screened first for novel secretory leader sequences which can mediate secretion of yeast invertase; and second, for the full-length cDNAs containing those novel secretory leader sequences. In this way novel secreted proteins are selected using a method which requires neither a bioassay nor knowledge of homology with other proteins.

Invertase genes appropriate for use in the method of the invention must encode only a nonsecreted enzyme. Preferably, the DNA encoding the invertase secretory leader sequence is removed. More preferably, the DNA encoding the invertase secretory leader sequence and the initiating methionine codon are removed. Most preferably, the DNA encoding the invertase secretory leader sequence, the initiating methionine and the first two codons (for methionine and serine) of the mature invertase protein are removed. Numerous methods for selective removal of DNA segments are known.

A nonsecreted invertase gene from any yeast species or strain may be used in the method of the invention. Preferably, the invertase gene from *Saccharomyces cerevisiae* strain S288C (ATCC accession number 26108) is modified as described above for use in the method of the invention. The DNA sequence of one unsecreted invertase gene (SUC2) is set forth in SEQ ID NO:1. The original cloning of the SUC2 gene is set forth in M. Carlson et al., Cell 28,145–154 (1982) and M. Carlson et al., Mol. Cell. Biol. 3, 439–447 (1983), incorporated herein by reference. The DNA sequence of the SUC2 invertase gene is available from GenBank, having the sequence name YSCSUC2.GB_PL and accession numbers V01311 and K00540. The SUC2 gene may also be isolated from yeast DNA using the GenBank sequence as the basis for constructing oligonucleotides for use in the polymerase chain reaction.

In accordance with the method of the invention, the nonsecreted yeast invertase gene is inserted into a suitable yeast expression vector. Numerous yeast expression vectors are known, for example, the YEp24 expression plasmid having ATCC accession number 37051 and GenBank sequence name YEP24.VEC; and the YRp17 expression plasmid having ATCC accession number 37078 and GenBank sequence name YRP17.VEC. An appropriate yeast expression vector for use in the present invention will contain a suitable yeast promoter and transcription terminator, for example the ADH1 promoter and transcription terminator as described in G. Ammerer, Methods in Enzymology 101, 192–201 (1983), incorporated herein by reference. Preferably, the promoter and transcription terminator are derived from the plasmid AAH5 described in Ammerer. The yeast expression vector will also contain a yeast origin of replication, preferably one which allows extrachromosomal replication; a selectable marker gene for selection of yeast transformants; an *Escherichia coli* origin of replication; and one or more *E. coli* drug resistance genes for selection of *E. coli* transformants. Any yeast origin of replication may be used, so long as it is capable of initiating DNA replication in yeast. Several yeast origins of replication are known, for example, the 2 μ origin, the autonomous replicating sequences (ARS) plus centromeres (CEN elements), and the like. Preferably, the 2 μ yeast origin of replication is used. Similarly, any yeast selectable marker gene may be used, so long as it allows growth only of the desired yeast transformants. Many such yeast selectable marker genes are known; for example URA3, TRP1, and LEU2. Preferably, the TRP1 yeast selectable marker gene is used in the method of the invention. Any *E. coli* origin of replication may be used, so long as it is capable of initiating DNA replication in *E. coli*. Many *E. coli* origins of replication are known, for example pMB1, colE1, and F. Preferably, the pUC *E. coli* origin of replication is used. Any *E. coli* drug resistance gene may be used, so long as it is capable of allowing growth only of the desired *E.coli* transformants. Many such *E. coli* drug resistance genes are known, for example the ampicillin resistance gene, the chloramphenicol resistance gene, and the tetracycline resistance gene. Preferably, the ampicillin resistance gene is used in the method of the invention.

In accordance with the method of the invention, the yeast expression vector containing the nonsecreted yeast invertase gene is ligated to a mammalian cDNA library using known methods. Numerous methods for generating mammalian cDNA libraries are known. For example, poly $A^+$ mRNA may be isolated from mammalian cells, purified and the corresponding cDNAs may be synthesized using reverse transcriptase, which is commercially available. Any kind of mammalian cell may be used as a source of mRNA. For example, peripheral blood cells may be used, or primary cells may be obtained from an organ, a developing embryo, a mature animal, a tissue, and the like, and such cells may be the source of mRNA for generation of a cDNA library. Cell lines such as the well known Chinese Hamster Ovary (CHO), COS monkey cell line, the Balb/c 3T3 murine cell line, lymphoid cell lines such as SP 2/0, hybridoma cell lines, and the like, may also be used as a source of mRNA for production of cDNA to construct a library in accordance with the method of the invention.

In the next step of the method of the invention, the ligated mammalian cDNA-yeast invertase gene is transformed into *E. coli* and recombinants isolated by selecting for drug resistance corresponding to the *E. coli* drug resistance gene on the yeast expression plasmid. Plasmid DNA is then isolated from about one million or more drug resistant *E. coli* recombinants and transformed into yeast strain which does not contain an invertase gene. Many such yeast strains are known, for example the YT455 strain (C. Kaiser et al., Mol. Cell. Biol. 6, 2382–2391 (1986), and yeast strain DA2100, having ATCC accession number 62625. Alternatively, a yeast strain which contains an invertase gene may be manipulated to delete that gene, for example, using methods set forth in *Current Protocols in Molecular Biology*, Eds. F. M. Ausubel, et al., Jolin Wiley & Sons (1990) in *Saccharomyces cerevisiae* chapters 13.2 and 13.3; or in F. Sherman et al., *Methods in Yeast Genetics*, Cold Spring Harbor Laboratory (Cold Spring Harbor, N.Y. 1979), both of which are incorporated herein by reference.

In accordance with the method of the invention, yeast recombinants are then selected using a selection pressure corresponding to the yeast selectable marker gene. The yeast recombinants are then collected in pools of about 100,000 to one million transformants and plated on yeast nutrient agar containing only sucrose or only raffinose as the carbon source. This selection will allow growth only of recombinants containing the yeast invertase gene ligated to a mammalian secretory leader sequence. Because invertase deficient yeast may grow on sucrose or raffinose, albeit at a low rate, the invertase selection may be repeated one or more times to maximize the selective pressure applied to the desired recombinants. When the desired number of yeast recombinants are obtained, they are pooled and DNA is isolated and transformed back into *E. coli* for analysis, e.g. by DNA sequencing. Alternatively, DNA may be isolated from individual yeast colonies and analyzed.

Novel mammalian secretory leader sequences obtained as described above are purified and used to screen a second cDNA library in the next step of the method of the invention. The second cDNA library is constructed in such a way as to contain full-length cDNAs, using known methods such as those described in *Current Protocols in Molecular Biology*, chapters 5.5 and 5.6 and in *Molecular Cloning, A Laboratory Manual*, Second Edition, J. Sambrook, et al., Cold Spring Harbor Laboratory Press (New York, 1989), chapter 8. The full-length cDNAs in the second cDNA library are then ligated to a mammalian expression vector such as the pED vector (Kaufman et al., Nucleic Acids Res. 19, 4484–4490 (1991); pEEF-BOS (Mizushima et al., Nucleic Acids Res. 18, 5322 (1990); pXM, pJL3 and pJL4 (Gough et al., EMBO J. 4, 645–653 (1985); and pMT2 (derived from pMT2-VWF, ATCC accession number 67122, see PCT/US87/00033). The second cDNA library which has been ligated to the mammalian expression vector is transformed into *E. coli*. The library may be screened by hybridization using known screening methods. Alternatively, plasmid DNA is iselated from the transformants for screening by hybridization or using PCR. When screened using PCR, the following general screening protocol may be followed: the cDNA clone containing the novel leader sequence is sequenced, and appropriate oligonucleotide primers are designed. From about one million *E. coli* transformants, pools of about 100,000 transformants are obtained by spreading pools of 10,000 transformants onto 150 mm plates and replicating the pool onto filters. Plasmid DNA is isolated from each pool and PCR is performed using the oligonucleotide primers based on the novel leader sequence. Specific DNA sequences are detected, for example, by gel electrophoresis of the DNA with or without hybridization. Each of the pools is similarly analyzed, and positive pools are subdivided and purified by hybridizing radioactive oligonucleotides directly to the filters as described in Chapter 6 of *Current Protocols in Molecular Biology* and in Chapter 1 of *Molecular Cloning: A Laboratory Manual*.

Using the method set forth above, novel full-length mammalian cDNA clones may be isolated and expressed in transient expression systems such as COS cells grown in a culture medium suitable for growth of cells and production of protein. The novel full-length cDNA clones may also be expressed in stable expression systems such as Chinese hamster ovary cells grown in a culture medium suitable for growth of cells and production of protein. In this way the novel secreted and extracellular proteins of the invention encoded by the mammalian cDNAs are produced which may then be assayed for biological activity in a variety of in vitro assays. In addition to detecting novel secreted proteins the method of the invention also detects and allows isolation of integral membrane proteins for example, receptors, and of proteins which transverse the endoplasmic reticulum to localize in intracellular organelles. The novel secreted proteins produced in accordance with the invention may be purified using known methods. For example, the novel secreted protein is concentrated using a commercially available protein concentration filter, such as an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the novel secreted protein from culture supernatant may also include one or more column steps over such affinity resins as lectin-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the novel secreted protein. Some or all of the foregoing purification steps, in various combinations, can also be employed to provide a substantially homogeneous isolated recombinant protein. The novel secreted protein thus purified is substantially free of other mammalian proteins.

I claim:

1. A method of screening for a cDNA encoding a novel secreted mammalian protein which comprises:

a) constructing a cDNA library from mammalian cellular RNA;

b) ligating said cDNA library to a DNA encoding a nonsecreted yeast invertase;

c) transforming the ligated DNA into *E. coli*;

d) isolating DNA containing mammalian cDNA ligated to the DNA encoding the nonsecreted yeast invertase from the transformed *E. coli* of step c);

e) transforming the DNA of step d) into a yeast cell which does not contain an invertase gene;

f) selecting yeast cells capable of growth on sucrose or raffinose;

g) purifying DNA from the yeast cells of step f);

h) analyzing the DNA obtained from step g) to determine its sequence and to determine whether it contains a novel sequence;

i) screening a second cDNA library to detect a full-length cDNA which contains the novel sequence of step h);

j) isolating the full-length cDNA of step i) wherein the isolated cDNA encodes a putative secreted mammalian protein.

* * * * *

UNITED STATES PATENT AND TRADEMARK OFFICE
CERTIFICATE OF CORRECTION

PATENT NO. : 5,536,637

DATED : July 16, 1996

INVENTOR(S) : Kenneth Jacobs

It is certified that error appears in the above-identified patent and that said Letters Patent is hereby corrected as shown below:

Claim 1, column 8, in step "f)", after "selecting", insert --transformed--; after "yeast cells", insert --from step e) which are--

Signed and Sealed this

Seventeenth Day of September, 1996

Attest:

BRUCE LEHMAN

Attesting Officer

Commissioner of Patents and Trademarks